US006284852B1

(12) United States Patent
Lynn et al.

(10) Patent No.: US 6,284,852 B1
(45) Date of Patent: Sep. 4, 2001

(54) ACID ACTIVATION OF RUTHENIUM METATHESIS CATALYSTS AND LIVING ROMP METATHESIS POLYMERIZATION IN WATER

(75) Inventors: David M. Lynn, Pasadena, CA (US); Eric L. Dias, Chapel Hill, NC (US); Robert H. Grubbs, South Pasadena, CA (US); Bernard Mohr, Heidelberg (DE)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/183,025

(22) Filed: Oct. 29, 1998

Related U.S. Application Data

(60) Provisional application No. 60/064,405, filed on Oct. 30, 1997.

(51) Int. Cl.[7] .............................. C08G 61/06; C07C 6/04
(52) U.S. Cl. .......................... 526/171; 526/92; 526/135; 526/145; 526/146; 526/147; 526/259; 526/268; 526/281; 526/283; 526/308; 526/309; 526/335; 526/336; 525/269; 525/280; 525/289; 525/290; 525/297; 585/638; 585/639; 585/641; 585/643; 585/645; 585/940
(58) Field of Search .............................. 526/92, 135, 145, 526/146, 147, 171, 281, 283, 308, 309, 259, 268, 335, 336; 525/269, 289, 290, 297, 280; 585/638, 639, 641, 643, 645, 940

(56) References Cited

U.S. PATENT DOCUMENTS

| | | | |
|---|---|---|---|
| 5,312,940 | 5/1994 | Grubbs et al. | 556/136 |
| 5,710,298 | 1/1998 | Grubbs et al. | 556/22 |
| 5,831,108 | 11/1998 | Grubbs et al. | 556/21 |
| 6,020,443 | * 2/2000 | Woodson et al. | 526/171 X |

OTHER PUBLICATIONS

Lynn, David M., et al., "Living Ring–Opening Metathesis Polymerization in Aqueous Media Catalyzed by Well–Defined Ruthenium Carbene Complexes", J. Am. Chem. Soc., vol. 118, pp. 784–790 (1996). no month.

Lynn, David M., et al., "Living Ring–Opening Metathesis Polymerization in Water via Activation of Water–Soluble Ruthenium Alkylidenes", Arnold and Mabel Beckman Laboratory of Chemical Synthesis, Division of Chemistry and Chemical Engineering, California Institute of Technology, Pasadena, CA 91125, Polymer Preprints, vol. 39, pp. 278–279 (1998). no month.

Mohr, Bernhard, et al., "Synthesis of Water–Soluble, Aliphatic Phosphines and Their Application to Well–Defined Ruthenium Olefin Metathesis Catalysts", Organometallics, vol. 15, No. 20, pp. 4317–4325 (1996). no month.

Bazan, Guillermo C., et al., "Living Ring–Opening Metathesis Polymerization of 2,3–Difunctionalized 7–Oxanorbornenes and 7–Oxanorbornadienes by $Mo(CHCMe_2R)(N-2,6-C_6H_3-i-Pr_2)(O-t-Bu)_2$ and $Mo(CHCMe_2R)(N-2,6-C_6H_3-i-Pr_2)(O-CMe_2CF_3)_2$", J. Am. Chem. Soc., vol. 113, pp. 6899–6907 (1991). no month.

Bazan, G.C., et al., "Living Ring–Opening Metathesis Polymerization of 2,3–Difunctionalized Norbornadienes by $Mo(CH-t-Bu)(N-2,6-C_6H_3-i-Pr_2)(O-t-Bu)_2$ ", J. Am. Chem. Soc., vol. 112, pp. 8378–8387 (1990). no month.

Nishikawa, Tomotaka, et al., "Evidence for Living Radical Polymerization of Methyl Methacrylate with Ruthenium Complex: Effects of Protic and Radical Compounds and Reinitiation from the Recovered Polymers", Macromolecules, vol. 30, No. 8, pp. 2244–2248 (1997). no month.

Tallarico, John A., et al., "Ring–Opening Metathesis. A Ruthenium Catalyst Caught in the Act", J. Am. Chem. Soc., vol. 119, pp. 7157–7158 (1997).

Manning, David D., et al., "Neoglycopolymer Inhibitors of the Selectins", Tetrahedron, vol. 53, No. 35, pp. 11937–11952 (1997).

Novak, B.M., et al., "The Development of Well–Defined Catalysts for Ring–Opening Olefin Metathesis Polymerization (ROMP)", Advances in Polymer Science, vol. 102, pp. 47–72 © Springer–Verlag Berlin Heidelberg 1992.

Schrock, Richard R., et al., "Synthesis of Molybdenum Imido Alkylidene Complexes and Some Reactions Involving Acyclic Olefins", J. Am. Chem. Soc., vol. 112, pp. 3875–3886 (1990).

Lynn, David M., et al., "Living Ring–Opening Metathesis Polymerization in Water", J. Am. Chem. Soc., vol. 120, pp. 1627–1628 (1998).

* cited by examiner

*Primary Examiner*—Fred Teskin
(74) *Attorney, Agent, or Firm*—Pillsbury Winthrop LLP; Tanuja V. Garde

(57) ABSTRACT

Activation of ruthenium based catalyst compounds with acid to improve reaction rates and yields of olefin metathesis reactions, including ROMP, RCM, ADMET and cross-metathesis reactions is disclosed. The ruthenium catalyst compounds are ruthenium carbene complexes of the general formula $A_xL_yX_zRu=CHR'$ where x=0, 1 or 2, y=0, 1 or 2, and z=1 or 2 and where R' is hydrogen or a substituted or unsubstituted alkyl or aryl, L is any neutral electron donor, X is any anionic ligand, and A is a ligand having a covalent structure connecting a neutral electron donor and an anionic ligand. The use of acid with these catalysts allows for reactions with a wide range of olefins in a variety of solvents, including acid-initiated RIM processes and living ROMP reactions of water-soluble monomers in water.

76 Claims, No Drawings

ACID ACTIVATION OF RUTHENIUM METATHESIS CATALYSTS AND LIVING ROMP METATHESIS POLYMERIZATION IN WATER

This application claims the benefit of U.S. Provisional Application No. 60/064,405, filed Oct. 30, 1997, which is incorporated herein by reference.

The U.S. Government has certain rights in this invention pursuant to Grant No. CH 9509745 awarded by the National Science Foundation and Grant No. GM 31332 awarded by the National Institutes of Health.

BACKGROUND OF THE INVENTION

1. Field of the Invention

The invention relates to highly active and stable ruthenium metal carbene complex compounds and their use as catalysts for olefin metathesis reactions.

2. Description of the Related Art

The formation of carbon-carbon bonds via olefin metathesis is of considerable interest and commercial utility, and considerable research efforts have been undertaken to develop olefin metathesis catalysts and systems. Group VIII transition metal catalysts have proven to be particularly useful for catalyzing olefin metathesis reactions, such as ring-opening metathesis polymerization (ROMP), ring-closing metathesis polymerization (RCM), acyclic diene metathesis (ADMET), and cross metathesis reactions. Both classical and well-defined olefin metathesis catalysts based on ruthenium have been shown to exhibit good tolerance to a variety of functional groups, as has been reported by, e.g., Grubbs, R. H. J. M. S.-Pure Appl. Chem. 1994, A31(11), 1829–1833; Aqueous Organometallic Chemistry and Catalysis. Horvath, I. T., Joo, F. Eds; Kluwer Academic Publishers: Boston, 1995; Novak, B. M.; Grubbs, R. H. J. Am. Chem. Soc. 1988, 110, 7542–7543; Novak, B. M.; Grubbs, R. H. J. Am. Chem. Soc. 1988, 110, 960–96; Nguyen, S. T.; Johnson, L. K.; Grubbs, R. H. J. Am. Chem. Soc. 1992, 114, 3974–3975 and Schwab, P.; Grubbs, R. H.; Ziller, J. W. J. Am. Chem. Soc. 1996, 118, 100, each of which is incorporated herein by reference. In particular, as reported by Lynn, D. M.; Kanaoka, S.; Grubbs, R. H. J. Am. Chem. Soc. 1996, 118, 784 and by Mohr, B.; Lynn, D. M.; Grubbs, R. H. Organometallics 1996, 15, 4317–4325, both of which are incorporated herein by reference, the robust nature of the ruthenium-carbon bonds in these complexes has enabled olefin metathesis reactions to be carried out in protic media. However, slow reaction rates and low yields have limited the application of these catalysts for a variety of olefin monomers and reaction conditions.

As an example, there is a need for homogeneous polymerization systems that are living in water and that will polymerize water-soluble monomers. In living polymerization systems, polymerization occurs without chain transfer or chain termination, giving greater control over polydispersity of the resultant polymers. Such polymerization systems are highly desirable as they would allow the controlled synthesis of water-soluble polymers and would enable precise control over the composition of block copolymers for use, for example, in biomedical applications. However, such polymerization systems represent a formidable challenge. For example, the addition of water to traditional living anionic or cationic systems results in rapid termination. The advent of late transition metal catalysts tolerant of numerous polar and protic functionalities has recently enabled living ring-opening metathesis polymerizations (ROMP), free-radical polymerizations, and isocyanide polymerizations in aqueous environments, as reported by Lynn, D. M.; Kanaoka, S.; Grubbs, R. H. J. Am. Chem. Soc. 1996, 118, 784; Manning, D. D.; Strong, L. E.; Hu, X.; Beck, P.; Kiessling, L. L. Tetrahedron, 1997, 53, 11937–11952; Manning, D. D.; Hu, X.; Beck, P.; Kiessling, L. L. J. Am. Chem. Soc. 1997, 119, 3161–3162; Nishikawa, T; Ando, T; Kamigaito, M; Sawamoto, M. Macromolecules 1997, 30, 2244–2248; Deming, T. J.; Novak, B. M. Polym. Prepr. (Am. Chem. Soc., Div. Polym. Chem.) 1991, 32, 455–456; and Deming, T. J.; Novak, B. M. Macromolecules, 1991, 24, 326–328, each of which is incorporated herein by reference. Although these examples represent significant advances toward entirely aqueous systems, the catalysts themselves are insoluble in water and the polymerization reactions basically occur in "wet" organic phases.

Aqueous ring-opening metathesis polymerization of strained, cyclic olefins initiated by Group VIII salts and coordination complexes is well-documented. Although these complexes serve as robust polymerization catalysts in water, the polymerizations are not living and inefficient initiation steps produce erratic results (typically less than 1% of metal centers are converted to catalytically-active species) and results in poor control over polymer molecular weight.

We recently reported the synthesis of well-defined, water soluble ruthenium alkylidenes which serve as excellent initiators for olefin metathesis reactions in water, methanol, and aqueous emulsions. See Mohr, B.; Lynn, D. M.; Grubbs, R. H. Organometallics, 1996, 15, 4317–4325, incorporated herein by reference. Further investigation of these complexes, however, revealed that potential applications could be limited by relatively fast termination reactions. Similar ruthenium alkylidene complexes are disclosed in U.S. Pat. Nos. 5,312,940 and 5,342,909 and U.S. application Ser. Nos. 08/693,789, filed Jul. 31, 1996, now U.S. Pat. No. 5,836,108, and Ser. No. 08/708,057, filed Aug. 30, 1996, now U.S. Pat. No. 5,710,298, each of which is incorporated herein by reference.

For these reasons, there is a need for well-defined olefin metathesis catalysts and systems with improved efficiencies that provide for increased reaction rates, increased product yields, and that allow for metathesis of a wider range of olefins in a broader range of solvents than previously possible.

SUMMARY OF THE INVENTION

The present invention meets the above and other needs and is directed to the use of acid to activate and enhance ruthenium-based metathesis catalysts for olefin metathesis, including ring-opening metathesis polymerization (ROMP) of strained and unstrained cyclic olefins, and ring-closing metathesis (RCM), acyclic diene metathesis (ADMET), and cross metathesis reactions of acyclic olefins.

In one embodiment of the invention, the ruthenium catalyst compounds are ruthenium carbene complexes of the general formula $A_xL_yX_zRu=CHR'$ where x=0, 1 or 2, y=0, 1 or 2, and z=1 or 2, and where R is hydrogen or a substituted or unsubstituted alkyl or aryl, L is any neutral electron donor, X is any anionic ligand, and A is a ligand having a covalent structure connecting a neutral electron donor and an anionic ligand. In other embodiments of the invention, the ruthenium catalyst compounds have the general formulas: $A_2LRu=CHR'$, $ALXRu=CHR'$ and $L_2X_2Ru=CHR'$.

These ruthenium catalysts contain acid-labile ligands and the addition of inorganic or organic acids to olefin metathesis reactions employing these catalysts results in substantially enhanced activities relative to systems in which acid is not present. Substantial rate increases in the presence of acid have been observed for olefin metathesis reactions in aqueous, protic and organic solvents in methods according to the present invention.

In another aspect of the invention, acid is used to activate ruthenium alkylidene complexes that are otherwise unreactive with olefins. This aspect of the invention allows for greater control in reaction injection molding (RIM) processes, as the catalyst and monomer can be stored together, either in solution or in neat monomer, and then acid is added to initiate polymerization. Similar processes can be applied to photoinitiated-ROMP (PROMP) systems and to photomasking applications using photoacid generators (photoacid generators are compounds that are not themselves acids, but which break down into acids and other products upon exposure to light energy).

The invention is further directed to living polymerization reactions taking place in aqueous solutions in the absence of any surfactants or organic cosolvents. In another embodiment of the invention, water-soluble ruthenium alkylidene complexes initiate living ROMP of water-soluble monomers in the presence of acid.

DETAILED DESCRIPTION OF THE INVENTION

In general, transition metal alkylidenes are deactivated or destroyed in polar, protic species. The ruthenium alkylidenes of the present invention are not only stable in the presence of polar or protic functional groups or solvents, but the catalytic activities of these alkylidenes enhanced by the deliberate addition of specific amounts of acid not present as a substrate or solvent. A number of ruthenium alkylidenes of the present invention are otherwise inactive absent the addition of acid to the reaction mixture. Such acidic conditions would destroy alkylidenes based on earlier transition metals.

Ruthenium alkylidenes of the present invention include alkylidenes of the general formula $A_xL_yX_zRu=CHR'$ where x=0, 1 or 2, y=0, 1 or 2, and z=1 or 2, and where R' is hydrogen or a substituted or unsubstituted alkyl or aryl, L is any neutral electron donor, X is any anionic ligand, and A is a ligand having a covalent structure connecting a neutral electron donor and an anionic ligand. These alkylidenes have enhanced catalytic activities in the presence of acid for a variety of olefin metathesis reactions, including but not limited to ROMP, RCM, ADMET and cross-metathesis and dimerization reactions. Preferred ruthenium alkylidenes are of the general formulas $A_2LRu=CHR'$, $ALXRu=CHR'$ and $L_2X_2Ru=CHR'$.

Olefin monomers that can be reacted according to the processes of the present invention include acyclic olefins, cyclic olefins, both strained and unstrained, and dienes. Unsaturated polymers may also be reacted according to the proccesses of the present invention. These olefins can be functionalized as well, and can include functional groups either as substituents of the olefins or incorporated into the carbon chain of the olefin. These functional groups can be, for example, alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate or sulfonate groups.

Both organic and inorganic acids are useful in enhancing catalytic activity of our catalysts, the preferred acids being HI, HCl, HBr, $H_2SO_4$, $H_3O^+$, $HNO_3$, $H_3PO_4$, $CH_3CO_2H$ and tosic acid, most preferably HCl. Acids may be added to the catalysts either before or during the reaction with olefin, with longer catalyst life generally observed when the catalyst is introduced to an acidic solution of olefin monomer. The acid or the catalyst can be dissolved in a variety of suitable solvents, including protic, aqueous or organic solvents or mixtures thereof. Preferred solvents include aromatic or halogenated aromatic solvents, aliphatic or halogenated organic solvents, alcoholic solvents, water or mixtures thereof. Of the aromatic solvents, the most preferred is benzene. Dichloromethane is most preferred of the halogenated aliphatic solvents; methanol is most preferred of the alcoholic solvents. Alternatively, the acid or the catalyst or both can be dissolved into neat olefin monomer.

In addition to the above acids, an alternative embodiment of the invention, photoacid generators that are converted to acids upon exposure to light energy may be used to activate or enhance the reaction. For example, UV curing of dicyclopentadiene (DCPD) to yield poly(DCPD) by photoinitiated-ROMP (PROMP) is readily accomplished as photoacid generators may be stored with both monomer and catalyst until metathesis is initiated through irradiation.

The preferred substituents of catalysts of the present invention are as follows. The neutral electron donor L is preferably a phosphine of the formula $PR^3R^4R^5$ where $R^3$ can be a secondary alkyl or cycloalkyl, and $R^4$ and $R^5$ can be an aryl, $C_1-C_{10}$ primary alkyl, secondary alkyl, or cycloalkyl, each independent of the other. More preferably, L is either P(cyclohexyl)$_3$, P(cyclopentyl)$_3$, P(isopropyl)$_3$, or P(phenyl)$_3$. The anionic ligand X is preferably hydrogen, or a halogen, or a unsubstituted or substitued moiety where the moiety is a $C_1-C_{20}$ alkyl, aryl, $C_1-C_{20}$ alkoxide, aryloxide, $C_3-C_{20}$ alkyldiketonate, aryldiketonate, $C_1-C_{20}$ carboxylate, arylsulfonate, $C_1-C_{20}$ alkylsulfonate, $C_1-C_{20}$ alkylthio, $C_1-C_{20}$ alkylsulfonyl, or $C_1-C_{20}$ alkylsulfinyl. In the case of substituted moiety, the substitution is $C_1-C_5$ alkyl, halogen, $C_1-C_5$ alkoxy, unmodified phenyl, halogen substituted phenyl, $C_1-C_5$ alkyl substituted phenyl, or $C_1-C_5$ alkoxy substituted phenyl.

A first preferred embodiment of the catalyst has the formula:

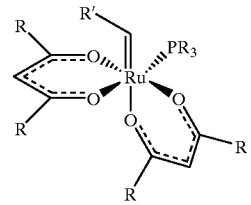

where each R is an aryl or alkyl, substituted or unsubstituted, and is preferably either a $C_1-C_{20}$ alkyl, an aryl, a substituted $C_1-C_{20}$ alkyl (substituted with an aryl, halide, hydroxy, $C_1-C_{20}$ alkoxy, or $C_2-C_{20}$ alkoxycarbonyl) or a substituted aryl (substituted with a $C_1-C_{20}$ alkyl, aryl, hydroxyl, $C_1-C_5$ alkoxy, amino, nitro, halide or methoxy). In the most preferred form, R is methyl or t-butyl, $PR_3$ is P(cyclohexyl)$_3$ and R' is phenyl.

A second preferred embodiment of the catalyst has the formula:

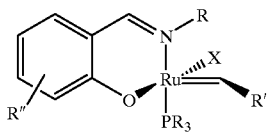

where R" is hydrogen, alkyl, halo, nitro or alkoxy, X is Cl, Br, I, $CH_3CO_2$ or $CF_3CO_2$ and each R is a substituted or unsubstituted alkyl or aryl, preferably either a $C_1$–$C_{20}$ alkyl, an aryl, a substituted $C_1$–$C_{20}$ alkyl (substituted with an aryl, halide, hydroxy, $C_1$–$C_{20}$ alkoxy, or $C_2$–$C_{20}$ alkoxycarbonyl) or a substituted aryl (substituted with a $C_1$–$C_{20}$ alkyl, aryl, hydroxyl, $C_1$–$C_5$ alkoxy, amino, nitro, halide or methoxy). In the most preferred form, R' is phenyl, R" is nitro, $PR_3$ is $P(cyclohexyl)_3$, X is Cl and R is aryl or aryl substituted with 2,6-diisopropyl groups.

A third preferred embodiment of the catalyst has the formula:

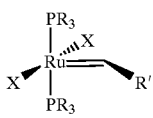

where $PR_3$ is either $P(cyclohexyl)_3$, $P(cyclopentyl)_3$, $P(isopropyl)_3$, or $P(phenyl)_3$ and X is Cl, Br, I, $CH_3CO_2$ or $CF_3CO_2$.

A fourth preferred embodiment of the catalyst has the formula:

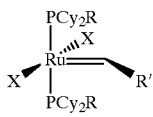

where Cy is cyclohexyl, X is Cl, Br, I, $CH_3CO_2$ or $CF_3CO_2$, and R is one of the following:

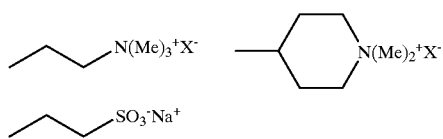

Preferred forms of this fourth embodiment have the following formulas:

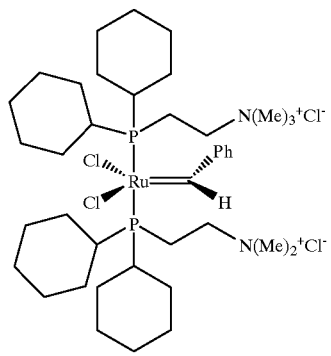

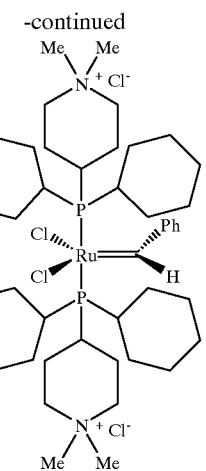

The catalysts of this fourth embodiment are highly effective when used in either aqueous or alcoholic solvents.

The ruthenium alkylidene compounds of the present invention may be synthesized using diazo compounds, by neutral electron donor ligand exchange, by cross metathesis, using aceytelene, using cumulated olefins, and in a one-pot method using diazo compounds and neutral electron donors according to methods described in U.S. Pat. Nos. 5,312,940, 5,342,909, 5,831,108 and 5,710,298, and in Chang, S., Jones, L., II, Wang, C., Henling, L. M., and Grubbs, R. H., Organometallics, 1998, 17, 3460–3465, Schwab, P., Grubbs, R. H., Ziller, J. W., J. Am. Chem. Soc. 1996, 118, 100–110, and Mohr, B., Lynn, D. M. and Grubbs, R. H., Organometallics, 1996, 15, 4317–4325, each of which is incorporated herein by reference in its entirety, and to methods further described herein.

The following non-limiting examples further illustrate the present invention:

EXAMPLE 1

Synthesis of Ruthenium Alkylidenes

General Considerations. All manipulations and reactions involving ruthenium alkylidenes were performed in a nitrogen-filled drybox or by using standard Schlenk techniques under an atmosphere of argon.

Synthesis of $RuCl_2(=CH-Ch=CPh_2)(PPh_3)_2$

Inside a dry box a solution of $RuCl_2(PPh_3)_4$ (6.0 g, 4.91 mmol) in a Schenk flask was reacted with 3,3-diphenylcyclopropene (954 mg, 1.0 eq) in a 1:1 mixture of $CH_2Cl_2/C_6H_6$. The flask was capped with a stopper, removed from the box, attached to a reflux condenser under argon and heated at 53° C. for 11 h. A fte r allowing the solution to cool to room temperature, all the solvent was removed in vacuo to give a dark yellow-brown solid. Benzene (10 ml) was added to the solid and subsequent swirling of the mixture broke the solid into a fine powder. Pentane (80 ml) was then slowly added to the mixture via cannula while stirring vigorously. The mixture was stirred at room temperature for 1 h and allowed to settle before the supernatant was removed via cannula filtration. This washing procedure was repeated two more times to ensure complete removal of all phosphine by-products. The resulting solid was then dried overnight to afford 4.28 g (98%) of $RuCl_2(=CH-Ch=CPh_2)(PPh_3)_2$ as a yellow powder with a slight green tint.

Synthesis of RuCl$_2$(=CHPh)(PR$_3$)$_2$ Complexes

RuCl$_2$(=CHPh)(PPh$_3$)$_2$. A solution of RuCl$_2$(PPh$_3$)$_3$ (2.37 g, 2.47 mmol) in CH$_2$Cl$_2$ (20 mL) was treated at −78° C. with a −50° C. solution of phenyldiazomethane (584 mg, 4.94 mmol, 2.0 equiv) in CH$_2$Cl$_2$ or pentane (3 mL). A spontaneous color change from orange-brown to brown-green and vigorous bubbling was observed. After the cooling b ath was removed, the solution was stirred for 5 min and the solution was then concentrated to ~3 mL. Upon addition of pentane (2 0 mL), a green solid was precipitated which was separated from the brown mother-liquid via cannula filtration, dissolved in CH$_2$Cl$_2$ (3 mL). and reprecipitated with pentane. This procedure was repeated until the mother-liquid was nearly colorless. The remaining gray-green microcrystalline solid was dried under vacuum for several hours. Yield=1.67 g (89%).

One-Pot Synthesis of RuCl$_2$(=CHPh)(PCy$_3$)$_2$. A solution of RuCl$_2$(PPh$_3$)$_3$ (4.0 g, 4.17 mmol) in CH$_2$Cl$_2$ (40 mL) was treated at −78° C. with a −50° C. solution of phenyldiazomethane (986 mg. 8.35 mmol, 2.0 equiv) in pentane (10 mL). Upon additioi. of the diazo compound, an instantaneous color change from orange-brown to green-brown and vigorous bubbling was observed. After the reaction mixture was stirred at −70° C. to −60° C. for 5–10 min, an ice-cold solution of tricyclohexylphosphine (2.57 g. 9.19 mmol, 2.2 equiv) in CH$_2$Cl$_2$ was added via syringe. Accompanied by a color change from brown-green to red. the solution was allowed to warm to room temperature and stirred for 30 min. The solution was filtered, concentrated to half of the volume, and filtrated. Methanol (100 mL) was added to precipitate a purple microcrystalline solid, which was filtered off, washed several times with acetone and methanol (10-mL portions), and dried under vacuum for several hours. Yield=3.40 g (99%).

One-pot Synthesis of RuCl$_2$(=CHPh)(PCp$_3$)$_2$. RuCl$_2$(=CHPh)(PCp$_3$)$_2$ is obtained was obtained by methods analogous to those used for the one-pot synthesis of RuCl$_2$(=CHPh)(PCy$_3$)$_2$, as a purple microcrystalline solid, using RuCl$_2$(PPh$_3$)$_3$ (4.00 g, 4.17 mmol), phenyldiazomethane (986 mg, 8.35 mmol, 2.0 eq.), and tricyclopentyl-phosphine (2.19 g, 9.18 mmol, 2.2 eq.). Due to the better solubility of the compound, methanol was used for the washings. Yield 2.83 g (92%). $^1$H NMR (CD$_2$Cl$_2$): δ 20.20 (s, Ru=CH), $^{31}$P NMR (CD$_2$Cl$_2$): δ 29.96 (s, PCp$_3$). Anal. Calcd. for C$_{37}$H$_{60}$Cl$_2$P$_2$Ru: C, 60.15; H, 8.19. Found: C, 60.39; H, 8.21.

Synthesis of (PCy$_3$)(+Bu$_2$acac)$_2$Ru(=CHPh)

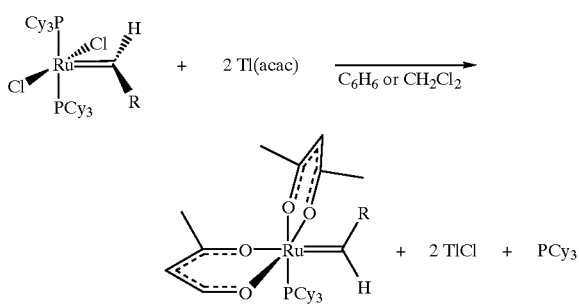

Inside the dry box, 200 mg (0.243 mmol) of RuCl$_2$(=CHR)(PCy$_3$)$_2$ prepared as above were weighed into a Schlenk flask and dissolved in approximately 120 ml of C$_6$H$_6$ and 150 mg of Tl(acetyl acetonate) (0.494 mmol, 2.03 eq) were added. The flask was capped with a rubber septum, removed from the dry box, and stirred for 1–2 hrs under argon on a Schlenk line, during which time the solution turned green. The solvent was removed in vacuo, and the solids were washed with hexanes (3×5 ml) to extract the product and PCy$_3$. The filtrate was collected via cannula filtration in another Schlenk flask, and the solvent was removed in vacuo.

Inside the dry box, the product mixture was dissolved in benzene, and 100 mg of CuCl (1.01 mmol, 4 eq) were added. The suspension was placed back on the Schlenk line and stirred for 2 hrs, and the solvent was removed in vacuo. The product was extracted from the CuCl.PCy$_3$ polymer with cold hexanes (3×5 ml). The filtrate was collected via cannula filtration, and the solvent removed in vacuo, leaving a green powder. $^1$H NMR (C$_6$D$_6$): δ 19.35 (d, 1 H, Ru=CH, $^3$J$_{HP}$=12 Hz), 8.59 (d, 2 H, H$_{ortho}$, $^3$J$_{HH}$=8.0 Hz), 7.47 (t, 1 H, H$_{para}$, $^3$J$_{HH}$=7.3 Hz), 7.37 (app t, 2 H, H$_{meta}$, $^3$J$_{HH}$=8.0, 7.3 Hz), 5.58 (s, 1 H), 4.76 (s, 1 H), 2.18 (s, 3 H), 2.12 (s, 3 H), 1.80 (s, 3 H), 1.67 (s, 3 H), 1.20–2.00 (m, 33 H), $^{31}$P($^1$H) NMR: δ 38.86 (s).

Synthesis of (PCy$_3$)(t-Bu$_2$acac)$_2$Ru(=CHPh)

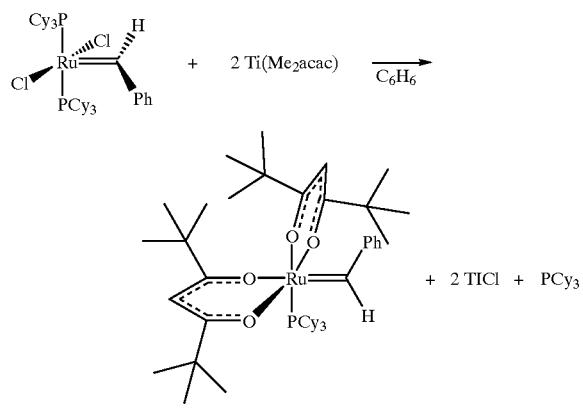

Inside the dry box, 100 mg (0.12 mmol) of RuCl$_2$(=CHPh)(PCy$_3$)$_2$ prepared as above were weighed into a Schlenk flask and dissolved in approximately 10 ml of C$_6$H$_6$ and 94 mg of Tl (t-Bu$_2$-acetyl acetonate) (0.24 mmol, 2 eq) were added. The flask was capped with a rubber septum, removed from the dry box, and stirred for 2 days under argon on a Schlenk line, during which time the solution turned green. The solvent was removed in vacuo, and the solids were washed with hexanes (3×5 ml) to extract the product and PCy$_3$.

The filtrate was collected via cannula filtration in another Schlenk flask, and the solvent was removed in vacuo.

Inside the dry box, the product mixture was dissolved in benzene, and 100 mg of CuCl (1.01 mmol, 8 eq) were added. The suspension was placed back on the Schlenk line and stirred for 2 hrs, and the solvent was removed in vacuo. The product was extracted from the CuCl.PCy$_3$ polymer with cold hexanes (3×5 ml). The filtrate was collected via cannula filtration, and the solvent removed in vacuo, leaving a light green powder. $^1$H NMR: δ 19.04 (d, 1 H, Ru=CH, $^3$J$_{HP}$=12 Hz), 8.28 (d, 2 H, H$_{ortho}$, $^3$J$_{HH}$=8.0 Hz), 7.56 (T, 1 H, H$_{para}$, $^3$J$_{HH}$=8.0 Hz), 7.31 (t, 2 H, H$_{meta}$, $^3$J$_{HH}$=8.0 Hz), 5.75 (s, 1 H), 5.11 (s, 1 H), 1.15 (app s, 18 H), 1.10 (s, 9 H), 0.82 (s, 9 h), 1.10–2.10 (m, 33 H), 31P{1H} NMR: δ 37.90 (s).

Synthesis of Schiff-base-Substituted Ru Complexes

Schiff-base substituted Ru complexes were prepared by first condensing salicylaldehydes with aliphatic or aromatic amine derivatives. The resulting ligands were converted to thallium salts and then substitution reactions were performed with $RuCl_2(=CHPh)(Cy_3)_2$. Successful Schiff-base ligands were prepared according to the procedures described below using the following pairs salicylaldehydes and amine derivatives: salicylaldehyde and 2,6-diisopropylaniline, 5-nitrosalicylaldehyde and 2,6-diisopropylaniline, 5-nitrosalicylaldehyde and 2,6-dimethyl-4-methoxyaniline, 5-nitrosalicylaldehyde and 4-bromo-2,6-dimethylaniline, 5-nitrosalicylaldehyde and 4-amino-3,5-dichlorobenzotrifluoride, 3-methyl-5-nitrosalicylaldehyde and 2,6-diisopropylaniline, and 5-nitrosalicylaldehyde and 2,6-diisopropyl-4-nitroaniline.

General Procedure for the Preparation of Schiff-base Ligands. The condensation of salicylaldehydes with aliphatic or aromatic amine derivatives was carried out with stirring in ethyl alcohol at 80° C. for 2 h. Upon cooling to 0° C., a yellow solid precipitated from the reaction mixture. The solid was filtered, washed with cold ethyl alcohol, and then dried in vacuo to afford the desired salicylaldimine ligand in excellent yields.

General Procedure for the Preparation of Thallium Salts. To a solution of Schiff bases in benzene or THF (10 mL) was added dropwise a solution of thalium ethoxide in benzene or THF (5 mL) at room temperature. Immediately after the addition, a pale yellow solid formed and the reaction mixture was stirred for 2 h at room temperature. Filtration of the solid under a nitrogen or argon atmosphere gave the thallium salts in quantitative yields. The salts were immediately used in the next step without further purification.

General Procedure for Preparation of Schiff-base-Substituted Ru Complexes. To a solution of $RuCl_2(=CHPh)(Cy_3)_2$ prepared as above in THF (5 ml) was added a solution of thallium salt prepared as above in THF (5 ml). The reaction mixture was stirred at room temperature for 3 h. After evaporation of the solvent, the residue was dissolved in a minimal amount of benzene and cooled to 0° C. The thallium chloride (byproduct of the reaction) was removed via filtration. The desired complex was then washed with cold benzene (10 ml×3), and the filtrate was evaporated. The solid residue was recrystallized from pentane (−70° C.) to give the Schiff-base-substituted Ru complexes in moderate to good yields as brown solids.

Synthesis of $RuCl_2(=CHPh)[Cy_2PCH_2CH_2N(CH_3)_3{}^+Cl]_2$ $RuCl_2(=CHPh)[Cy_2PCH_2CH_2N(CH_3)_3{}^+Cl]_2$ was prepared by placing dicyclohexylphosphine (19.7 g, 0.99 mol) in THF (100 mL) into a Schlenk flask equipped with a stirbar, capped with a rubber septum, and purging with argon. The solution was cooled to 0° C., and $BH_3\cdot THF$ (100 mL of a 1.0 M solution in THF, 0.1 mol, 1.01 equiv) was slowly added via cannula. The colorless solution was stirred for 2 h at 0° C. and then allowed to warm to room temperature. Evaporation of the solvent resulted in a crystalline white solid, $Cy_2PH(BH_3)$, which was recrystallized from pentane. (Yield: 18.9 g (90%) as white needles).

The $Cy_2PH(BH_3)$ (4 g, 18.90 mmol) was dissolved in THF (100 mL) and was placed into a Schlenk flask and purged with argon. The solution was cooled to −78° C., and n-butyllithium (12.4 mL of a 1.6 M solution in hexane, 19.80 mmol, 1.05 equiv) was added dropwise via syringe over a period of 10 min. The colorless reaction mixture was stirred for 2 h while slowly warming to room temperature. Upon cooling of the solution to −78° C., 2-chloro-N,N-dimethylaminoethane (2.44 g, 22.70 mmol, 1.20 equiv) in THF (50 mL) was slowly added via syringe. The reaction mixture was kept for 2 h at −78° C. and then stirred at room temperature overnight. Evaporation of the solvent gave a white solid which was subjected to column chromatography (silica gel/methanol, $R_1=0.25$) to yield 3.48 g (65%) of $Cy_2P(BH_3)CH_2CH_2N(CH_3)_2$, as a white solid.

1.50 g (5.30 mmol) of $Cy_2P(BH_3)CH_2CH_2N(CH_3)_2$ was dissolved in ether (60 mL) followed by addition of methyl iodide (1.88 g, 13.24 mmol, 2.5 equiv). The reaction mixture was stirred for 4 h at room temperature, during which a white solid precipitated. The precipitate was collected by filtration, washed with ether and dried in vacuo to yield 2.17 g (97%) of $Cy_2P(BH_3)CH_2CH_2N(CH_3)_3{}^+I^-$, as a white solid.

The $Cy_2P(BH_3)CH_2CH_2N(CH_3)_3{}^+I^-$, (1.50 g, 3.53 mmol) was then dissolved in morpholine (30 mL), placed into a Schlenk flask and purged with argon. The reaction mixture was stirred for 2 h at 110° C. and then cooled to room temperature. Evaporation of the solvent gave a gummy white residue which was dissolved in a small mount of methanol (3 mL) and reprecipitated by addition of cold THF (25 mL). The supernatant was removed via cannula filtration, and the precipitate was washed with a small amount of THF (5 m) and dried in vacuo to yield 1.05 g (72%) of $Cy_2PCH_2CH_2N(CH_3)_3{}^+I^-$ as a white crystalline solid.

$RuCl_2(=CHPh)(PPh_3)_2$ (1.20 g, 1.53 mmol) prepared as above was then placed in a Schlenk flask equipped with a stirbar, capped with a rubber septum, and purged with argon. $CH_2Cl_2$ (15.0 ml) was added, and the dark green solution was cooled to −78° C. $Cy_2PCH_2CH_2N(CH_2)_3{}^+I^-$ (1.0 g., 3.13 mmol, 2.05 equiv) was dissolved in methanol (10 mL) under argon, cooled to 78° C., and slowly added to the Schlenk flask via syringe. The reaction mixture was stirred at −78° C. for 30 min while a color change to dark red was observed. Stirring was continued for 30 min as the reaction warmed to room temperature. Removal of the solvent in vacuo yielded a dark purple solid. The solid material was dissolved in $CH_2Cl_2$ (10 mL) and stirred, and pentane (100 mL) was added to precipitate a purple solid. The brownish red supernatant was removed and discarded via cannula filtration, and this procedure was repeated until the supernatant became colorless. By this stage, the solid product was insoluble in $CH_2Cl_2$ and was further treated with heat $CH_2Cl_2$, until the washings became colorless. The product was dissolved in methanol (15 mL) and cannula filtered from an insoluble dark purple material, and solvent was removed in vacuo to yield the desired product $RuCl_2(=CHPh)[Cy_2PCH_2CH_2N(CH_3)_3{}^+Cl]_2$ as a purple solid (0.680 g, 67.4%). Although the [M+] peak was not observed in the FAB mass spectrum, the observed isotopic abundance for corresponding [M+H−Cl−] peaks identically matched the predicted isotope pattern for the [M+H−Cl−] fragment of $RuCl_2(=CHPh)[Cy_2PCH_2CH_2N(CH_3)_3{}^+C]_2$.

Synthesis of $RuCl_2(=CHPh)[Cy_2P(N,N-dimethylpiperidinium\ chloride)]_2$.

$RuCl_2(=CHPh)[Cy_2P(N,N-dimethylpiperidinium\ chloride)]_2$ was prepared as follows. Lithiation of $Cy_2PH(BH)_3$ with n-butylithium (10.0 mL of a 1.6 M solution in hexane, 16.0 mmol. 1.06 equiv) was performed as described above. Upon cooling of the solution to −78° C., 6 (2.0 g. 7.42 mmol. 0.5 equiv) in THF (50 mL) was slowly added via syringe. The reaction mixture was maintained at −78° C. for 2 h and then stirred at 60° C. for 6 h. Upon evaporation of the solvent ether (50 mL) and saturated aqueous sodium bicarbonate solution (50 mL) were added. The organic phase was separated and the aqueous phase extracted with ether (2×100 mL). Evaporation of the combined organic layers gave a white solid which was subjected to column chromatography (silica gel/methanol, $R_f$=0.22) to yield 1.25 g (54%) of a white solid. This solid was then methylated with methyl iodide, analogous to method described above for the methylation of $Cy_2PCH_2CH_2N(CH_2)_3{}^+I^-$ to yield $Cy_2P(BH_3)(N,N\text{-dimethylpiperidinium iodide})$ as a white solid (98%), which was then converted with morpholine to yield $Cy_2P(N,N\text{-dimethylpiperidinium iodide})$ as a white solid (73%), again by a method analogous to that described above for the conversion of $Cy_2PCH_2CH_2N(CH_2)_3{}^+I^-$ to $Cy_2PCH_2CH_2N(CH_2)_3{}^+I^-$.

$RuCl_2(PPh_3)_3$ (1.38 g, 1.44 mmol) prepared as above was placed in a Schlenk flask and purged with argon. $CH_2Cl_2$ (15.0 mL) was added, and the dark red solution was cooled to $-78°$ C. Phenyldiazomethane (0.340 g, 2.88 mmol, 2.0 equiv) was quickly weighed under air, dissolved in pentane (1.0 mL), cooled to $-78°$ C., and added to the Schlenk flask via pipet under an argon purge. Upon addition of the diazo compound, an instantaneous color change from dark red to dark green was observed. The reaction was stirred for 5 min. and a solution of $Cy_2P(N,N\text{-dimethylpiperidinium iodide})$ (1.10 g, 3.18 mmol, 2.2 equiv) in methanol (10 mL) was added via syringe. The solution became dark-red, and stirring was continued for 30 min as the reaction warmed to room temperature. Solvent was removed in vacuo and dried overnight to yield a burgundy solid. The solid material was dissolved in $CH_2Cl_2$ (15 mL) and stirred, and pentane (100 mL) was added to precipitate a burgundy solid. Pentane should be added quickly, as 19 slowly decomposes in $CH_2Cl_2$. The dark red supernatant was removed and discarded via cannula filtration, and the product was reprecipitated until the supernatant was colorless. The solid was dissolved in $CH_2Cl_2$ (10 mL), precipitated by addition of the THF (150 mL) and cannula filtered. This process continued until the supernatant was colorless. The product was dissolved in methanol (10 mL) and cannula filtered from insoluble material, and solvent was removed in vacuo to yield the desired $RuCl_2(=CHPh)[Cy_2P(N,N\text{-dimethylpiperidinium chloride})]_2$ product as a burgundy solid.

EXAMPLE 2

Synthesis of Olefin Monomers

Synthesis of exo-N-(N',N',N'-trimethylammonio)ethyl-bicyclo[2.2.1]hept-5-ene-2,3-dicarboximide chloride Exo-bicyclo[2.2.1]hept-5-ene-2,3-dicarboxylic anhydride (2.03 g, 12.37 mmol) and N,N-dimethylethylenediamine (1.09 g, 12.37 mmol) were dissolved in $CH_2Cl_2$ (30 mL) and heated at 90° C. for 8 hours in a heavy-walled sealed tube. Upon cooling to room temperature, this solution was washed with brine (3X), the organic layer was dried over sodium sulfate, and the solvent was removed in vacuo. This white crystalline product was dissolved in THF (20 mL) and subsequently treated with 5 equivalents of methyl iodide at room temperature. The resulting white precipitate was filtered, washed liberally with THF, and dried under vacuum to yield the title compound as an iodide salt. Iodide/chloride ion exchange as previously described[3] afforded 3 as a white flaky solid (34% yield based on anhydride starting material). $^1$H NMR δ ($CD_3OD$): 6.38 (s, 2H), 4.0 (t, J=7.05 Hz, 2H), 3.54 (t, J=7.2 Hz, 2H), 3.25 (s, 2H), 3.22 (s, 9H), 2.90 (s, 2H), 1.37 (dd, J=9.9 Hz, J=9.9 Hz, 2H). $_{13}$C NMR δ ($CD_3OD$): 177.53, 137.26, 61.86, 52.29, 47.54, 44.73, 42.07, 31.60.

Synthesis of exo-N-(N',N',N'-trimethylammonio)ethyl-bicyclo-7-oxabicyclo[2.2.1]hept-5-ene-2,3-dicarboximide chloride In a three-necked round bottom flask under an atmosphere of nitrogen, exo-7-oxabicyclo[2.2.1]hept-5-ene-2,3-dicarboxylic anhydride (4.0 g, 24.07 mmol) and N,N-dimethylethylenediamine (3.17 g, 35.98 mmol) were dissolved in toluene (40 mL). Magnesium sulfate (8.0 g) was added to this solution and the reaction was heated at 60° C. for 23 hours. Upon cooling to room temperature, the reaction mixture was filtered and washed with water (4X). The organic layer was dried over sodium sulfate and the solvent was removed in vacuo. This white crystalline product was dissolved in THF (15 mL) and subsequently treated with 2.1 equivalents of methyl iodide at room temperature. The resulting white precipitate was filtered, washed liberally with THF, and dried under vacuum to yield the title compound as an iodide salt. Iodide/chloride exchange as previously described[3] afforded 4 as a white flaky solid (14% yield based on anhydride starting material). $^1$H NMR δ ($CD_3OD$): 6.56 (s, 2H), 5.19 (s, 2H), 3.94 (t, J=6.0 Hz, 2H), 3.58 (t, J=6.44 Hz, 2H), 3.18 (s, 9H), 3.00 (s, 2H). 13C NMR δ ($CD_3OD$): 176.58, 136.34, 81.03, 62.28, 52.59, 52.50, 32.49.

EXAMPLE 3

Acid Activation of ROMP of DCPD

Ruthenium catalysts 1–5 prepared as in Example 1 show enhanced activities for the ROMP of high- and low-strained cyclic olefins, the RCM and ADMET of multiply-unsaturated substrates, and the acyclic cross metathesis of linear olefins in the presence of acids.

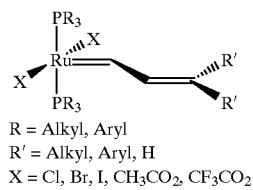

1

R = Alkyl, Aryl
R' = Alkyl, Aryl, H
X = Cl, Br, I, $CH_3CO_2$, $CF_3CO_2$

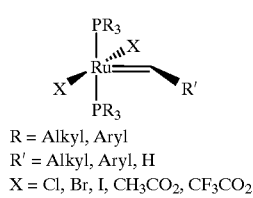

2

R = Alkyl, Aryl
R' = Alkyl, Aryl, H
X = Cl, Br, I, $CH_3CO_2$, $CF_3CO_2$

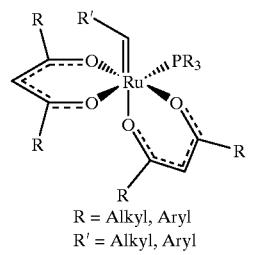

3

R = Alkyl, Aryl
R' = Alkyl, Aryl

-continued

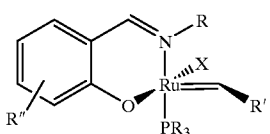

R = Alkyl, Aryl
R' = Alkyl, Aryl, H
R" = Alkyl

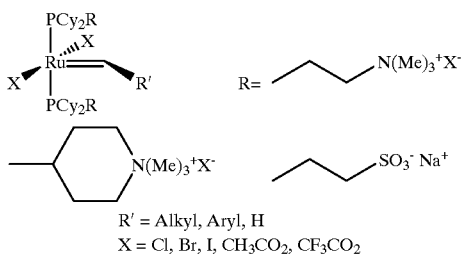

R' = Alkyl, Aryl, H
X = Cl, Br, I, CH$_3$CO$_2$, CF$_3$CO$_2$

Typical polymerization reactions were conducted in the following manner. In a nitrogen-filled drybox, monomer was added to a NMR tube or a vial equipped with a teflon-coated stirbar and capped with a rubber septum. The ruthenium alkylidene catalysts were added to a second vial and the vial was capped with a rubber septum. Outside the drybox, water or methanol was added to each vial via syringe, and the polymerization was initiated by transferring the catalyst solution to the vial containing the monomer.

The addition of acid to ruthenium catalysts 1–5 results in faster catalyst turnover and increased yields for reactions with olefins that are otherwise slow, incomplete, or not reactive. This enhanced activity is observed in both protic solvents such as water or methanol (with complexes 3–5) and organic solvents (with complexes 1–4) with either stoichiometric or nonstoichiometric equivalents of strong or weak organic and inorganic acids. Acids may be added to the catalysts either before or during the reaction with olefin, with longer catalyst life observed when the catalyst is introduced to an acidic solution of olefin monomer. This allows the metathesis of a wider range of olefins in a broader range of solvents than previously possible.

Comparative results of ROMP reactions using complexes 3 and 4 with different monomers, in neat monomer or methanol, and in the presence and absence of HCl are tabulated in Table 1 below.

TABLE 1

| Complex | Monomer | Acid (HCl) | Solvent | Temp | Time | Yield (%) |
|---|---|---|---|---|---|---|
| 3 | DCPD | no | none | RT | days | 0 |
| 3 | DCPD | yes | none | RT | <1 min | 100 |
| 3 | 10 | no | MeOH | RT | days | 0 |
| 3 | 10 | yes | MeOH | RT | 15 min | 100 |
| 4 | DCPD | no | none | RT | days | 0 |
| 4 | DCPD | yes | none | RT | <1 min | 100 |

TABLE 1-continued

| Complex | Monomer | Acid (HCl) | Solvent | Temp | Time | Yield (%) |
|---|---|---|---|---|---|---|
| 4 | 10 | no | MeOH | RT | 12 h | 100 |
| 4 | 10 | yes | MeOH | RT | 15 min | 100 |

DCPD = dicyclopentadiene;

monomer 10 = 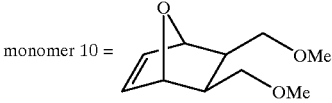

As seen from Table 1, complex 3 does not react at all with olefins in the absence of acid, and complex 4 reacts extremely slowly in the absence of acid. Upon addition of acid, reactions occur to 100% yield within minutes. Thus, complexes 3 and 4 can be stored in solution in the presence of olefin without reaction, and acid can be added as desired to initiate catalysis in a RIM-type process with strained, cyclic olefins such as dicyclopentadiene (DCPD). Additionally, UV curing of DCPD to yield poly(DCPD) by photoinitiated-ROMP (PROMP) is readily accomplished as photoacid generators may be stored with both monomer and catalyst until metathesis is initiated through irradiation.

EXAMPLE 4

Acid Activation in RIM Processes

Catalysts 1 and 2 of Example 3 are efficient catalysts for the bulk polymerization of both endo- and exo-dicyclopentadiene (DCPD), yielding a hard, highly-crosslinked material.

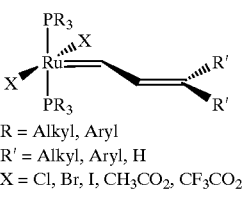

1

R = Alkyl, Aryl
R' = Alkyl, Aryl, H
X = Cl, Br, I, CH$_3$CO$_2$, CF$_3$CO$_2$

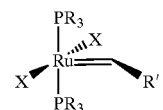

2

R = Alkyl, Aryl
R' = Alkyl, Aryl, H
X = Cl, Br, I, CH$_3$CO$_2$, CF$_3$CO$_2$

These catalysts are active enough, however, that polymerization ensues shortly after monomer and catalysts are mixed. On industrial scales, this can result in complete polymerization prior to injection of the reaction mixture into a mold. Catalysts 3 and 4 of Example 3, however, are unreactive toward DCPD in the absence, and can be stored indefinitely as a solution in DCPD monomer without appreciable decomposition of the catalyst or polymerization of the monomer:

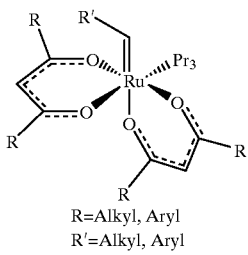

R=Alkyl, Aryl
R'=Alkyl, Aryl

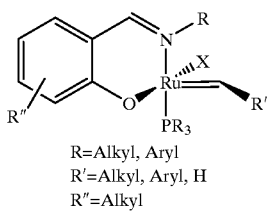

R=Alkyl, Aryl
R'=Alkyl, Aryl, H
R"=Alkyl

Upon addition of a strong inorganic acid or organic acid (particularly HCl) either as a gas, solid, or in a solution of water or organic solvent, these catalysts are activated, and polymerization ensues immediately.

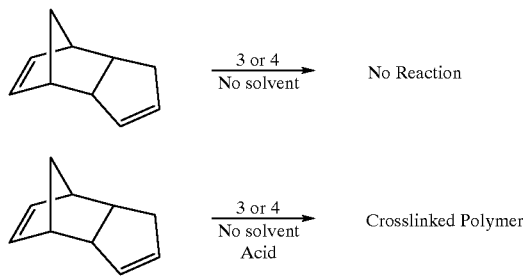

Thus, catalysts 3 and 4 can be stored with monomer, and be used in reaction-injection molding (RIM) processes through combination with another stream of monomer containing acid:

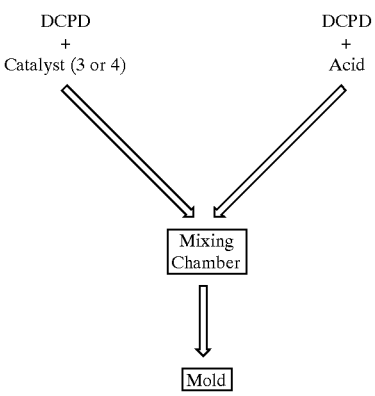

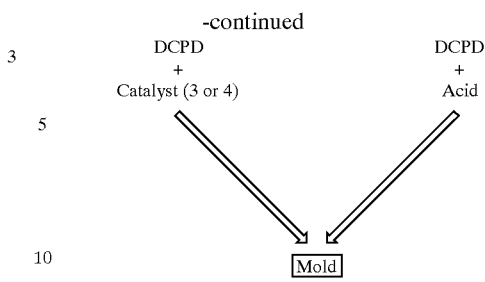

In addition, solutions of 3 or 4, monomer, and a photoacid generator can be stored together and used in photomasking applications through UV curing techniques.

EXAMPLE 5

Acid Activation of ROMP of Norbornenes

Acids can be used effectively to initiate the ROMP of other monomers with these catalysts in solution as well. For example, while solutions of functionalized norbornenes and 7-oxanorbornenes do not polymerize in the presence of catalysts 3 of Example 3, polymerization rapidly ensues upon addition of from 0.3 or more equivalents of acid. Such monomers will polymerize using catalysts 4 of Example 3, although initiation is very poor(<5%), even at elevated temperatures. In the presence of acid, however, these catalysts fully initiate, and reactions proceed to completion:

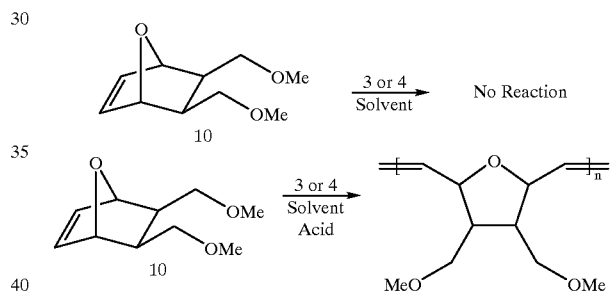

The results of the above reactions using catalysts 3 or 4 to polymerize monomer 10 in the presence or absence of HCl and with methanol as a solvent are shown in Table 2 below.

TABLE 2

| Complex | Monomer | Acid (HCl) | Solvent | Temp | Time | Yield (%) |
|---|---|---|---|---|---|---|
| 3 | 10 | no | MeOH | RT | days | 0 |
| 3 | 10 | yes | MeOH | RT | 15 min | 100 |
| 4 | 10 | no | MeOH | RT | 12 h | 100 |
| 4 | 10 | yes | MeOH | RT | 15 min | 100 |

Again, complex 3 does not react at all with the olefin in the absence of acid, and complex 4 reacts extremely slowly in the absence of acid. Upon addition of acid, reactions occur to 100% yield within minutes.

In addition, water-soluble catalyst 5 of Example 3 will also polymerize water-soluble norbornene and 7-oxanorbornene monomers in water and methanol, but the catalyst typically dies at low conversion. Addition of up to one equivalent of HO or DO to these reactions results in complete conversion of monomer and the rate of polymerization is doubled.

EXAMPLE 6

Acid Activation for Living ROMP in Water

In this example, activation in water with a strong Brønsted acid of alkylidene complexes $RuCl_2(=CHPh)[Cy_2P(N,N\text{-}dimethylpiperidinium\ chloride)]_2$ (complex 6 below) and $RuCl_2(=CHPh)[Cy_2PCH_2CH_2N(CH_3)_3{}^+Cl]_2$ (complex 7 below) (prepared as in Example 1) results in the quantitative conversion of functionalized monomers. In the presence of a Brønsted acid, complexes 6 and 7 quickly and quantitatively initiate the living polymerization

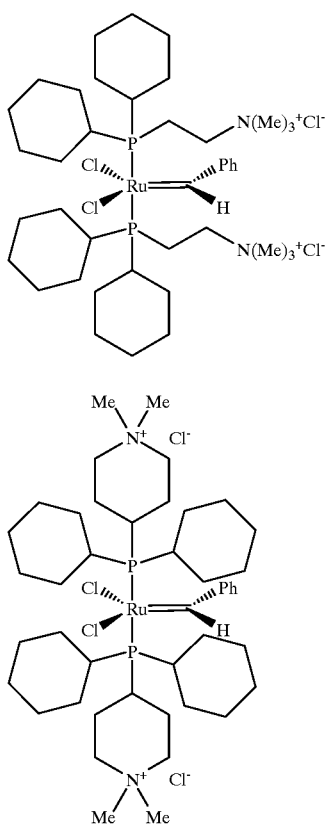

of water-soluble monomers in the absence of surfactant or organic solvents.

This result is a significant improvement over aqueous ROMP systems using "classical" aqueous ROMP catalysts. The propagating species in these reactions is stable, and the synthesis of water-soluble block copolymers was achieved via sequential monomer addition. Notably, the polymerizations are not living in the absence of acid. The effect of the acid in these systems appears to be twofold—in addition to eliminating hydroxide ions, which would cause catalyst decomposition; catalyst activity is also enhanced by protonation of phosphine ligands. Remarkably, the acids do not react with the ruthenium alkylidene bond.

Although alkylidenes 6 and 7 initiate the ROMP of functionalized norbornenes and 7-oxanorbornenes in aqueous solution quickly and completely (in the absence of acid), the propagating species in these reactions often decompose before polymerization is complete. For example, in the ROMP of water-soluble monomers exo-N-(N',N',N'-trimethylammonio)ethyl-bicyclo[2.2.1]hept-5-ene-2,3-dicarboximide chloride (monomer 13) and exo-N-(N',N',N'-trimethylammonio)ethyl-bicyclo-7-oxabicyclo[2.2.1]hept-5-ene-2,3-dicarboximide chloride (monomer 14) (prepared as in Example 2 above) initiated by alkylidene 6, conversions ranging from 45–80% are usually observed (Equation 1). Although these water-soluble complexes are similar to ruthenium alkylidenes which are very stable toward polar and protic functional groups in organic solvents, they appear to be susceptible to termination reactions when dissolved in water or methanol.

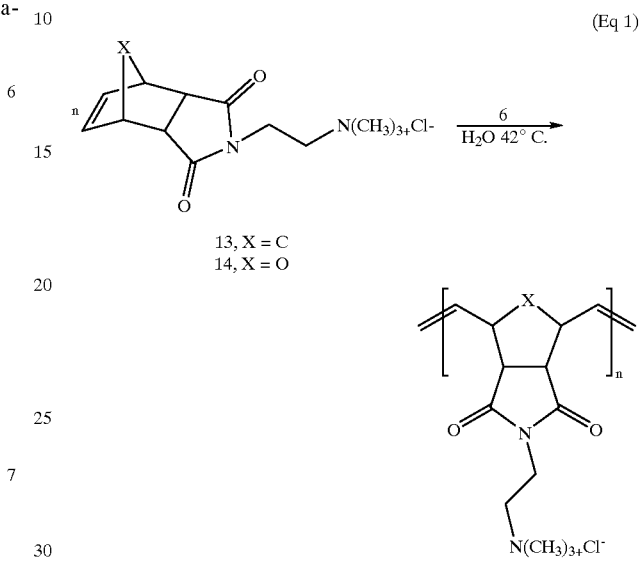

(Eq 1)

The results of the above reactions with catalysts 6 and 7, in the presence and absence of HCl is set forth in Table 3 below.

TABLE 3

| Complex | Monomer | Acid (HCl) | Solvent | Temp | Time | Yield (%) |
|---|---|---|---|---|---|---|
| 6 and 7 | 13 | no | $H_2O$ | 45 | 2 h | 45 |
| 6 and 7 | 13 | yes | $H_2O$ | 45 | 15 min | 100 |
| 6 and 7 | 14 | no | $H_2O$ | 45 | 2 h | 80 |
| 6 and 7 | 14 | yes | $H_2O$ | 45 | 15 m | 100 |

These results show that reaction times and yields are dramatically increased upon addition of acid to the reaction system.

EXAMPLE 7

Acid Generation of New Monophosphine Alkylidene in Living ROMP System

Consistent with data obtained for earlier "classical" aqueous ROMP systems, we determined that the presence of hydroxide ions in aqueous solutions of catalysts 6 and 7 of Example 8 resulted in rapid decomposition of the catalysts. In order to eliminate hydroxide ions that might result from the autoprotolysis of water or the basic nature of the phosphines employed, Brønsted acids were added to aqueous polymerization mixtures of monomers 13 and 14, catalysts 6 and 7, and water. Although reactions performed in mildly acidic solutions of $DCl/D_2O$ yielded no dramatic improvements, the monomers could be completely polymerized in cases where 0.3–1.0 equivalent of DCl (relative to alkylidene) was added. The presence of acid also had a profound effect on the reaction rate: the polymerizations were at least twice as fast as those to which no acid was added. More interestingly, a propagating alkylidene species was clearly observed by 1H NMR following complete consumption of monomer and addition of more monomer to the reaction mixture resulted in further quantitative polymerization.

To further investigate this effect, the reaction of DCl with 6 was studied in the absence of olefin. Upon addition of 0.3 equivalents of DCl to a $D_2O$ solution of 6, the acid cleanly protonated 0.3 equivalents of phosphine to yield a phosphonium salt and 0.3 equivalents of a new alkylidene species, instead of protonating the ru thenium-carbon double bond (Equation 2). The remarkable stability of the alkylidene bond in the presence of this very strong acid highlights the tolerance of ruthenium-based metathesis catalysts of the present invention toward protic functionalities.

tive initiating species outlined above. In fact, at ambient temperature, the propagating species in these reactions can be observed for well over one month.

In addition to the relatively low concentration of the monophosphine species dictated by the equilibrium in Equation 2, stability toward bimolecular decomposition is presumably imparted via the relative steric bulk of the propagating alkylidene. The $^1H$ NMR resonances for the two propagating alkylidenes coalesce at higher temperatures, indicating rapid equilibration via phosphine scrambling.

To probe the living nature of the aqueous polymerizations conducted in the presence of acid, an NMR-scale polymerization of monomer 13 was conducted employing DCl (1.0 equivalent relative to alkylidene), and the relative amount of propagating species was quantified via integration of the

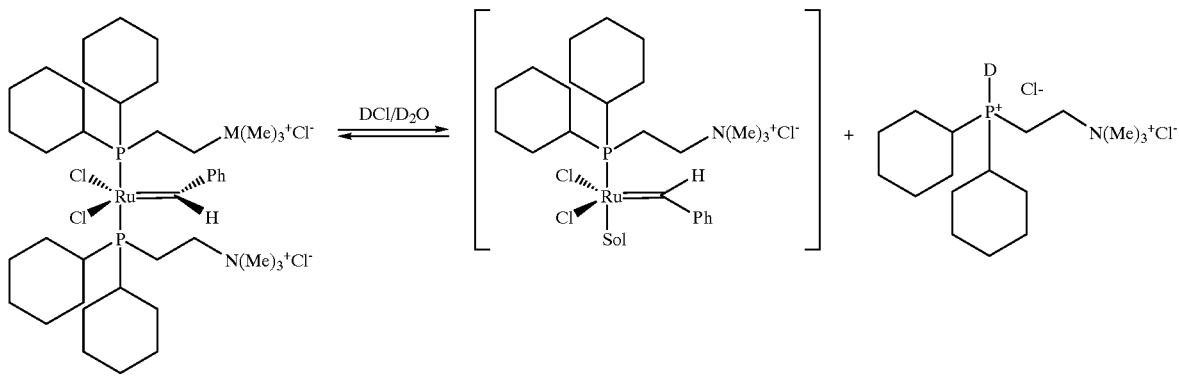

(Eq 2)

The new alkylidene generated upon addition of acid has been identified by $^1H$ and $^{31}P$ NMR spectroscopy as a monophosphine derivative of 6 such as that shown in Equation 2. In aqueous reactions employing up to one equivalent of acid, the monophosphine species is remarkably stable, presumably stabilized through coordination of water. Addition of excess phosphine to the reaction mixture up to 1.5 hours after addition of acid reverses the equilibrium, reforming 6 with less than 5% detectable decomposition. Protonation of phosphine in this manner is not stoichiometric. For instance, the addition 1.0 equivalent of DO yielded an equilibrium mixture of monophosphine and bisphosphine alkylidene species in a ratio of 1:2. The alkylidenes decomposed more rapidly under these conditions in the absence of monomer.

As anticipated, we found that monomers 13 and 14 could be completely polymerized when up to 1.0 equivalent of DO was added to the reaction mixture. Additionally, the presence of acid also had a profound effect on the reaction rate: the polymerizations were up to ten times faster than those to which no acid had been added. More significantly, two propagating alkylidene species were observed by $^1H$ NMR spectroscopy following complete consumption of monomer, and the addition of more monomer to the reaction mixture resulted in further quantitative polymerization. The direct observation of propagating species is important, as it allows the extent of chain termination, a key factor in defining a living system, to be easily and directly addressed throughout the course of the reaction.

The alkylidenes observed in the above reactions, corresponding to both bisphosphine and monophosphine propagating species, are significantly more stable than the respecalkylidene protons against the aromatic protons of the polymer endgroups. After 15 minutes at 45° C., the reaction was >95% complete and the relative integration of the alkylidene protons of the two propagating species (coalesced as a broad singlet at 19.2 ppm ) did not decrease either during the reaction or after all monomer had been consumed. In fact, the propagating species remained intact for an additional 15 minutes in the absence of monomer before slowly decomposing.

A block copolymerization of monomers 13 and 14 was carried out, via sequential monomer addition, to demonstrate the robust nature of the propagating species in these reactions. After complete polymerization of monomer 13, the reaction was allowed to sit for 5 minutes before 20 equivalents of monomer 14 were injected. Monomer 14 was rapidly and completely consumed, and the concentration of the propagating species remained constant both during and after the polymerization of the second block.

Within the limits of NMR sensitivity, the direct observation and quantification of the propagating alkylidenes in the above experiments demonstrates the absence of chain termination in these reactions. The fact that the alkylidene resonance does not disappear over a time period twice as long as the time scale of the reaction indicates that these systems are indeed living. Gel permeation chromatography (GPC) analysis of these polymers yields a symmetric, monomodal peak with a polydispersity index (PDI) of 1.2–1.5.

The equilibrium represented in Equation 2 provides a straightforward explanation for the rate enhancements, and thus the living nature, of the polymerizations described above. For alkylidene complexes of the present invention of the type $(PR_3)_2Cl_2Ru=CHR$, olefin metathesis has been shown to proceed through a mechanism in which a phosphine dissociates from the metal center. Rates of olefin metathesis in organic systems have been increased by the addition of phosphine scavengers, favoring the equilibrium for olefin coordination and phosphine dissociation, although the catalyst rapidly decomposes under these conditions. In aqueous systems employing complexes 6 and 7, protons act as phosphine scavengers, increasing the rate of olefin metathesis without concomitant acceleration of catalyst decomposition. The differences in the rates of propagation and termination under acidic conditions allows for rapid, quantitative conversion of monomer in a living manner.

EXAMPLE 8

ROMP of Unstrained Cylic Olefins and Metathesis of Acyclic Olefins

In contrast to the "classical" ruthenium metathesis catalysts mentioned above, which react only with highly-strained olefins, alkylidenes 6 and 7 of Example 6 also promote the ROMP of less-strained monomers such as 1,5-cyclooctadiene, and are active in the metathesis of acyclic olefins in protic solvents. For example, 6 will dimerize 1-hexene in methanol to give 5-decene in 20% yield (Equation 3). In these systems, separation of catalyst from product is facilitated through addition of water to the reaction mixture. Olefins collected from the resulting two-phase system contain very low levels of detectable ruthenium.

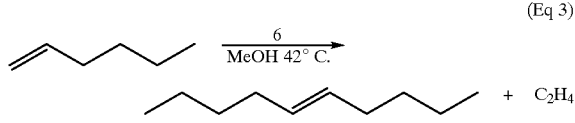

(Eq 3)

Although the invention has been described in some respects with reference to the above embodiments, many variations and modifications will be apparent to those skilled in the art. It is therefore the intention that the following summary not be given a restrictive interpretation, but rather should be viewed to encompass such variations and modifications that may be routinely derived from the inventive subject matter disclosed.

What is claimed is:

1. A process for performing an olefin metathesis reaction comprising:
    contacting an olefin monomer with an inorganic or organic acid and a ruthenium carbene complex of the formula:

wherein:
    x=0, 1, or 2;
    y=0, 1, or 2; and
    z=1 or 2;
    and wherein:
    R' is selected from the group consisting of hydrogen, alkyl, substituted alkyl, aryl and substituted aryl;
    L is any neutral electron donor;
    X is any anionic ligand; and
    A is a ligand having a covalent structure connecting a neutral electron donor and an anionic ligand.

2. The process of claim 1 wherein said acid is selected from the group consisting of HI, HCl, HBr, $H_2SO_4$, $H_3O^+$, $HNO_3$, $H_3PO_4$, $CH_3CO_2H$ and tosic acid.

3. The process of claim 1 wherein said acid is HCl.

4. The process of claim 1 wherein said acid is added to a solution comprising said olefin monomer and said ruthenium carbene complex.

5. The process of claim 1 wherein said acid is generated by irradiating a photoacid generator.

6. The process of claim 1 wherein the olefin metathesis reaction is conducted without a solvent.

7. The process of claim 1 wherein the olefin metathesis reaction is conducted in a solvent selected from the group consisting of protic solvents, aqueous solvents, organic solvents and mixtures thereof.

8. The process of claim 7 wherein the process is conducted in a solvent selected from the group consisting of aromatic solvents, halogenated aromatic solvents, aliphatic organic solvents, halogenated aliphatic organic solvents, alcoholic solvents, water and mixtures thereof.

9. The process of claim 8 wherein said solvent is selected from the group consisting of benzene, dichloromethane and methanol.

10. The process of claim 1 wherein L is a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

11. The process of claim 10 wherein L is selected from the group consisting of
    —P(cyclohexyl)$_3$, -P(cyclopentyl)$_3$, -P(isopropyl)$_3$, and -P(phenyl)$_3$.

12. The process of claim 1 wherein X is selected from the group consisting of hydrogen, halogen, and substituted or unsubstituted $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, wherein substituents are selected from a group consisting of $C_1$–$C_5$ alkyl, halogen, $C_1$–$C_5$ alkoxy, phenyl, halogen substituted phenyl, $C_1$–$C_5$ alkyl substituted phenyl, and $C_1$–$C_5$ alkoxy substituted phenyl.

13. The process of claim 1 wherein said ruthenium carbene complex is of the formula:

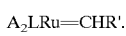

14. The process of claim 13 wherein L is a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

15. The process of claim 13 wherein L is selected from the group consisting of P(cyclohexyl)$_3$, P(cyclopentyl)$_3$, P(isopropyl)$_3$, and P(phenyl)$_3$.

16. The process of claim 13 wherein said ruthenium carbene complex is of the formula:

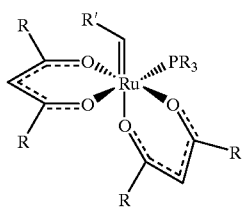

wherein each R is independently selected from the group consisting of alkyl, substituted alkyl, aryl or substituted aryl.

17. The process of claim 16 wherein each R is independently selected from the group consisting of (a) $C_1$–$C_{20}$ alkyl;

(b) aryl;

(c) $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and (d) aryl substituted with one or more groups selected from the group consisting of $C_1$–$C_{20}$ alkyl, aryl, hydroxyl, $C_1$–$C_5$ alkoxy, amino, nitro, halide and methoxy.

18. The process of claim 16 wherein

R is methyl or t-butyl, $PR_3$ is P(cyclohexyl)$_3$, and

R' is phenyl.

19. The process of claim 1 wherein said ruthenium carbene complex is of the formula:

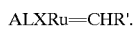

ALXRu=CHR'.

20. The process of claim 19 wherein L is a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

21. The process of claim 19 wherein L is selected from the group consisting of P(cyclohexyl)$_3$, P(cyclopentyl)$_3$, P(isopropyl)$_3$, and P(phenyl)$_3$.

22. The process of claim 19 wherein X is selected from the group consisting of hydrogen, halogen, and substituted or unsubstituted $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, wherein substituents are selected from a group consisting of $C_1$–$C_5$ alkyl, halogen, $C_1$–$C_5$ alkoxy, phenyl, halogen substituted phenyl, $C_1$–$C_5$ alkyl substituted phenyl, and $C_1$–$C_5$ alkoxy substituted phenyl.

23. The process of claim 19 wherein said ruthenium carbene complex is of the formula:

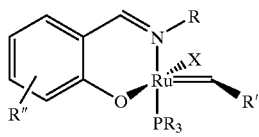

wherein each R is independently selected from the group consisting of alkyl, substituted alkyl, aryl and substituted aryl;

R" is selected from the group consisting of hydrogen, halo, nitro, and alkoxy; and X is selected from the group consisting of Cl, Br, I, $CH_3CO_2$ and $CF_3CO_2$.

24. The process of claim 23 wherein R is selected from the group consisting of (a) $C_1$–$C_{20}$ alkyl;

(b) aryl;

(c) $C_1$–$C_{20}$ alkyl substituted with one or more groups selected from the group consisting of aryl, halide, hydroxy, $C_1$–$C_{20}$ alkoxy, and $C_2$–$C_{20}$ alkoxycarbonyl; and (d) aryl substituted with one or more groups selected from the group consisting of $C_1$–$C_{20}$ alkyl, aryl, hydroxyl, $C_1$–$C_5$ alkoxy, amino, nitro, halide and methoxy.

25. The process of claim 23 wherein

R' is phenyl,

R" is nitro $PR_3$ is P(cyclohexyl)$_3$,

X is Cl, and

R is unsubstituted aryl or aryl substituted with a 2,6-diisopropyl group.

26. The process of claim 1 wherein said ruthenium carbene complex is of the formula:

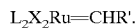

$L_2X_2Ru$=CHR'.

27. The process of claim 26 wherein L is a phosphine of the formula $PR^3R^4R^5$, wherein $R^3$ is selected from the group consisting of secondary alkyl and cycloalkyl, and $R^4$ and $R^5$ are each independently selected from the group consisting of aryl, $C_1$–$C_{10}$ primary alkyl, secondary alkyl, and cycloalkyl.

28. The process of claim 26 wherein L is selected from the group consisting of P(cyclohexyl)$_3$, P(cyclopentyl)$_3$, P(isopropyl)$_3$, and P(phenyl)$_3$.

29. The process of claim 26 wherein X is selected from the group consisting of hydrogen, halogen, and substituted or unsubstituted $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, wherein substituents are selected from a group consisting of $C_1$–$C_5$ alkyl, halogen, $C_1$–$C_5$ alkoxy, unmodified phenyl, halogen substituted phenyl, $C_1$–$C_5$ alkyl substituted phenyl, and $C_1$–$C_5$ alkoxy substituted phenyl.

30. The process of claim 26 wherein said ruthenium carbene complex is of the formula:

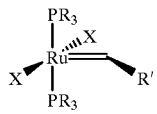

wherein $PR_3$ is selected from the group consisting of P(cyclohexyl)$_3$, P(cyclopentyl)$_3$, P(isopropyl)$_3$, and P(phenyl)$_3$ and wherein X is selected from the group consisting of Cl, Br, I, $CH_3CO_2$ and $CF_3CO_2$.

31. The process of claim 26 wherein said ruthenium carbene complex is of the formula:

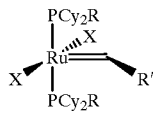

and wherein Cy is cyclohexyl and R is independently selected from the group

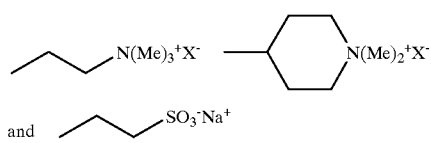

consisting of:

and wherein X is selected from the group consisting of Cl, Br, I, $CH_3CO_2$ and $CF_3CO_2$, and wherein the olefin metathesis reaction is conducted in an aqueous or alcoholic solvent or mixtures thereof.

32. The process of claim 31 wherein the ruthenium carbene complex is:

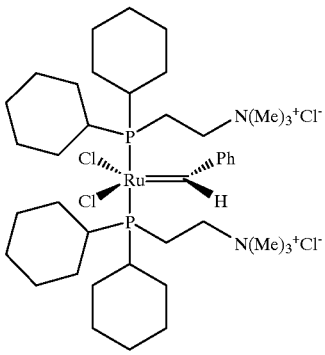

and wherein the olefin metathesis reaction is conducted in an aqueous or alcoholic solvent or mixtures thereof.

33. The process of claim 31 wherein the ruthenium carbene complex is:

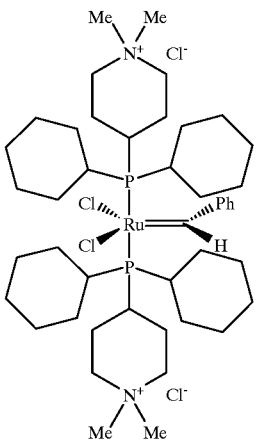

and wherein the olefin metathesis reaction is conducted in an aqueous or alcoholic solvent or mixtures thereof.

34. The process of claim 1 wherein said olefin metathesis reaction is selected from the group consisting of ring opening metathesis polymerization, ring closing metathesis, acyclic diene metathesis, and cross metathesis.

35. The process of claim 1 wherein said olefin monomer is selected from the group consisting of strained cyclic olefins, unstrained cyclic olefins, acyclic olefins, and dienes.

36. The process of claim 35 wherein said olefin monomer contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

37. The process of claim 1 wherein said reaction is ring-opening metathesis polymerization and said olefin monomer is a cyclic olefin.

38. The process of claim 37 wherein said cyclic olefin contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

39. The process of claim 38 wherein block copolymers are synthesized by sequential addition of a first cyclic olefin followed by the addition of a second cyclic olefin.

40. The process of claim 37 wherein (1) the acid is dissolved in a first solution containing said cyclic olefin monomer, (2) the ruthenium carbene complex is dissolved in a second solution containing said cyclic olefin monomer, and (3) then said first solution is added to a said second solution.

41. The process of claim 40 wherein said first and second solutions comprise neat olefin monomer.

42. The process of claim 40 wherein said first and second solutions comprise water.

43. The process of claim 37 wherein said cyclic olefin is selected from the group consisting of cyclobutene, cycloheptene, cyclooctene, cyclononene, cyclodecene, cyclooctadiene, cyclononadiene, cyclopentadiene and dicyclopentadiene and derivatives thereof.

44. The process of claim 43 wherein said cyclic olefin contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

45. The process of claim 37 wherein said cyclic olefin is selected from the group consisting of functionalized norbornenes and 7-oxanorbornenes.

46. The process of claim 37 wherein said cyclic olefin is selected from the group consisting of endo-dicyclopentadiene and exo-dicyclopentadiene.

47. The process of claim 1 wherein said olefin metathesis reaction is ring-closing metathesis and said olefin monomer is an acyclic diene.

48. The process of claim 47 wherein said acyclic diene contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

49. The process of claim 1 wherein said olefin metathesis reaction is acyclic diene metathesis or cross metathesis.

50. The process of claim 49 wherein said olefin monomer contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

51. The process of claim 49 wherein said olefin monomer is 1-hexene.

52. A process for performing a ring opening metathesis polymerization reaction comprising:

contacting a cyclic olefin monomer with an inorganic or organic acid and a ruthenium carbene complex of the formula:

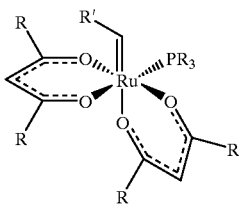

R' is selected from the group consisting of alkyl, substituted alkyl, aryl, and substituted aryl;

PR$_3$ is a phosphine of the formula PR$^3$R$^4$R$^5$ wherein R$^3$ is selected from the group consisting of secondary alkyl and cycloalkyl, and R$^4$ and R$^5$ are each independently selected from the group consisting of aryl, C$_1$–C$_{10}$ primary alkyl, secondary alkyl and cycloalkyl; and each remaining R is selected from the group consisting of alkyl, substituted alkyl, aryl, and substituted aryl.

53. The process of claim 52 wherein:

PR$_3$ is selected from the group consisting of P(cyclohexyl)$_3$, P(cyclopentyl)$_3$, P(isopropyl)$_3$, and P(phenyl)$_3$; and each remaining R is independently selected from the group consisting of
(a) C$_1$–C$_{20}$ alkyl;
(b) aryl;
(c) C$_1$–C$_{20}$ alkyl substituted with one or more groups selected from the group consisting of aryl, halide, hydroxy, C$_1$–C$_{20}$ alkoxy, and C$_2$–C$_{20}$ alkoxycarbonyl; and
(e) aryl substituted with one or more groups selected from the group consisting of C$_1$–C$_{20}$ alkyl, aryl, hydroxyl, C$_1$–C$_5$ alkoxy, amino, nitro, halide and methoxy.

54. The process of claim 52 wherein
R' is phenyl,
PR$_3$ is P(cyclohexyl)$_3$, and
R is methyl or t-butyl.

55. The process of claim 52 wherein said acid is HCl.

56. The process of claim 52 wherein said acid is added to a solution comprising said cyclic olefin monomer and said ruthenium carbene complex.

57. The process of claim 52 wherein said acid is generated by irradiating a photoacid generator.

58. The process of claim 52 wherein the ring opening metathesis polymerization reaction is conducted without a solvent.

59. The process of claim 52 wherein the ring opening metathesis polymerization reaction is conducted in a solvent selected from the group consisting of protic solvents, aqueous solvents, organic solvents and mixtures thereof.

60. The process of claim 52 wherein said cyclic olefin contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

61. The process of claim 60 wherein block copolymers are synthesized by sequential addition of a first cylic olefin followed by the addition of a second cyclic olefin.

62. The process of claim 52 wherein
(1) the acid is dissolved in a first solution containing said cyclic olefin monomer, (2) the ruthenium carbene complex is dissolved in a second solution containing said cyclic olefin monomer, and (3) then said first solution is added to a said second solution.

63. The process of claim 62 wherein said first and second solutions comprise neat olefin monomer.

64. The process of claim 62 wherein said first and second solutions comprise water.

65. The process of claim 52 wherein said cyclic olefin is selected from the group consisting of functionalized norbornenes and 7-oxanorbornenes.

66. The process of claim 52 wherein said cyclic olefin is selected from the group consisting of endo-dicyclopentadiene and exo-dicyclopentadiene.

67. A process for performing a ring opening metathesis polymerization reaction comprising:

contacting a cyclic olefin monomer with a ruthenium carbene complex of the formula:

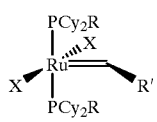

wherein:
Cy is cyclohexyl,
R is independently selected from the group consisting of:

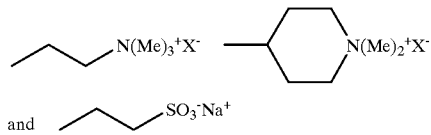

and X is selected from the group consisting of Cl, Br, I, CH$_3$CO$_2$ and CF$_3$CO$_2$, and wherein the ring opening polymerization reaction is conducted in the presence of an inorganic or organic acid and in an aqueous or alcoholic solvent or mixtures thereof.

68. The process of claim 67 wherein the ruthenium carbene complex is:

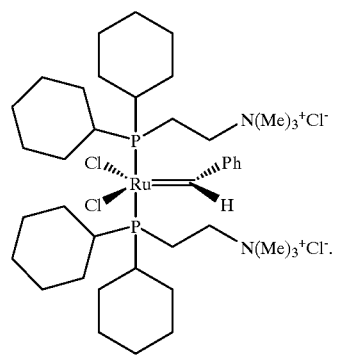

69. The process of claim 67 wherein the ruthenium carbene complex is:

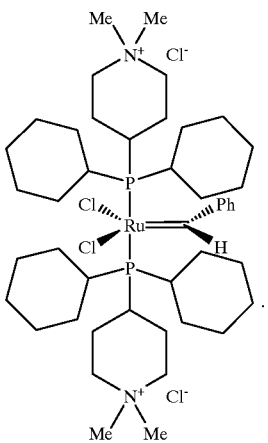

70. The process of claim 67 wherein said solvent is aqueous and said cyclic olefin is water-soluble.

71. The process of claim 67 wherein said acid is HCl.

72. The process of claim 67 wherein said acid is added to a solution comprising said cyclic olefin monomer and said ruthenium carbene complex.

73. The process of claim 67 wherein said cyclic olefin contains a functional group selected from the group consisting of alcohol, thiol, ketone, aldehyde, ester, disulfide, carbonate, imine, carboxyl, amine, amide, nitro acid, carboxylic acid, isocyanate, carbodiimide, ether, halogen, quaternary amine, carbohydrate, phosphate, sulfate and sulfonate.

74. The process of claim 73 wherein block copolymers are synthesized by sequential addition of a first cylic olefin followed by the addition of a second cyclic olefin.

75. The process of claim 67 wherein said cyclic olefin is selected from the group consisting of functionalized norbornenes and 7-oxanorbornenes.

76. A process for performing an olefin metathesis reaction comprising: contacting an unsaturated polymer with a ruthenium carbene complex of the formula:

$$A_xL_yX_zRu\!=\!CHR'$$

in the presence of inorganic or organic acid,
wherein:
  x=0, 1, or 2;
  y=0, 1, or 2; and
  z=1 or 2;
and wherein:
  R' is selected from the group consisting of hydrogen, alkyl, substituted alkyl, aryl and substituted aryl;
  L is any neutral electron donor;
  X is any anionic ligand; and
  A is a ligand having a covalent structure connecting a neutral electron donor and an anionic ligand.

* * * * *